US007015321B2

(12) United States Patent
Nicolaou et al.

(10) Patent No.: US 7,015,321 B2
(45) Date of Patent: Mar. 21, 2006

(54) SYNTHESIS OF NON-SYMMETRICAL SULFAMIDES USING BURGESS-TYPE REAGENTS

(75) Inventors: Kyriacos C. Nicolaou, La Jolla, CA (US); Deborah Longbottom, San Diego, CA (US); Scott A. Snyder, Carlsbad, CA (US); Xianhai Huang, Warren, NJ (US)

(73) Assignee: The Scripps Research Institute, La Jolla, CA (US)

( * ) Notice: Subject to any disclaimer, the term of this patent is extended or adjusted under 35 U.S.C. 154(b) by 253 days.

(21) Appl. No.: 10/685,658

(22) Filed: Oct. 14, 2003

(65) Prior Publication Data

US 2004/0138448 A1     Jul. 15, 2004

Related U.S. Application Data

(60) Provisional application No. 60/417,936, filed on Oct. 12, 2002.

(51) Int. Cl.
C07D 273/02    (2006.01)
C07D 273/08    (2006.01)
C07D 285/36    (2006.01)
C07D 285/16    (2006.01)
C07D 285/06    (2006.01)

(52) U.S. Cl. ............................ 540/489; 544/8; 548/127
(58) Field of Classification Search ................ 540/489; 544/8; 548/127
See application file for complete search history.

(56) References Cited

OTHER PUBLICATIONS

Lamberth, C. "Burgess Reagent ([Methoxycarbonylsulfamoyl]triethylammonium Hydroxide Inner Salt): Dehydrations and More" Journal für Praktische Chemie, vol. 342(5), pp. 518-522 (2000).*

Winum et al, "N-(tert-Butoxycarbonyl)-N-[4-(dimethylazaniumlidene-1,4-dihydropyridin-1-ylsulfonyl] azanide: A New Sulfamoylating Agent. Structure and Reactivity toward Amines" Organic Letters, vol. 3(14), pp. 2241-2243 (2001).*

Khapli et al, "Burgess Reagent in Organic Synthesis" Journal of the Indian Institute of Science, vol. 81(4), pp. 461-476 (Jul.-Aug. 2001).*

Atkins, Jr.; et al., "The Reactions of an N-Sulfonylamine Inner Salt", *J. Am. Chem. Soc. 90*: 4744-4745 (1968).

Burgess et al., "Synthetic Applications of N-Carboalkoxysulfamate Esters", *J. Am. Chem. Soc. 92*: 5224-5226 (1970).

Atkins, Jr.; et al., "Synthesis and Reactions of N-Sulfonylamines", *J. Am. Chem. Soc. 94*: 6135-6141 (1972).

Burgess, et al., "Thermal Reactions of Alkyl-N-Carbomethoxysulfamate Esters", *J. Org. Chem. 38*: 26-31 (1973).

Davis, et al., "A new Synthesis of Primary Amines from Diarylidenesulfamides", *Tetrahedron Lett. 27*: 3957-3960 (1986).

(Continued)

*Primary Examiner*—James O. Wilson
*Assistant Examiner*—Zachary C. Tucker
(74) *Attorney, Agent, or Firm*—Donald G. Lewis

(57) ABSTRACT

A practical and high-yielding method for the efficient, one-step synthesis of diverse classes of N,N'-differentiated sulfamides employs a wide range of amino alcohols and simple amines using Burgess-type reagents. This methodology extends the application and availability of sulfamides within the fields of chemical biology, medicinal chemistry, asymmetric synthesis, and supramolecular chemistry.

7 Claims, 7 Drawing Sheets

OTHER PUBLICATIONS

Rosenberg, et al., "Potent, Low Molecular Weight Renin Inhibitors Containing a C-Terminal Heterocycle: Hydrogen Bonding at the Active Site", *J. Med. Chem. 33*: 1582-1590 (1990).

Oppolzer, et al., "Enantiomerically Pure, Crystalline 'Anti'-Aldols from N-Acylbornanesultam: Aldolization and Structure of Intermediate t-butyldimethylsilyl-N,O-Ketene Acetal", *Tetrahedron Lett. 32*: 61-64 (1991).

Oppolzer, et al., "Enantiomerically Pure Isoxazolines via Addition of Nitrile Oxides to Chiral N-Acryloyl Toluene-2, α-Sultams", *Tetrahedron Lett. 32*: 4893-4896 (1991).

Sartor, et al., "Enantioselective Diels-Alder Reaction of Enals: Fighting Species Multiplicity of the Catalyst with Donor Solvents", *Tetrahedron Asymmetry 2*: 639-642 (1991).

Ahn, et al., "Asymmetric Aldol Reactions Employing a Cyclic Sulfamide Chiral Auxiliary", *Tetrahedron Lett. 33*: 6661-6664 (1992).

Castro, et al., "Synthesis and Biological Activity of 3-[2-(Dimethylamino)cthyl]-5-[(1, 1-dioxo-5-methyl-1,2,5-thiadiazolidin-2-yl)methyl]-H-indole and Analogues: Agonists for the 5-HT$_{1D}$ Receptor", *J. Med. Chem. 37*: 3023-3032 (1994).

Taibe, P,; Mobashery, S. "(Methoxycarbonylsulfamoyl) triethylammonium hydroxide", in Encyclopedia of Reagents for Organic Synthesis, vol. 5 (Ed. L. A. Paquette), John Wiley & Sons: Chichester, 1995, pp. 3345-3347.

Dewynter, et al., "Sulfonyl Bis-N-Oxazolidinone (SBO): A New Versatile Dielectrophile with Sequential Reactivity", *Tetrahedron Lett. 38*: 8691-8694 (1997).

Pansare, et al., "Stereoselective Synthesis of 3,4-Disubstituted 1,2,5-Thiadiazolidine 1,1-Dioxides and Their conversion to Unsymmetrical Vicinal Diamincs", *Synlett*: 623-624 (1998).

Tozer, et al., "4-Chlorobenzyl Sulfonamide and Sulfamide Derivatives of Histamine Homologues: The Design of Potent Histamine H$_3$ Receptor Antagonists", *Bioorg. Med. Chem. Lett. 9*: 3103-3108 (1999).

Gong et al., "Polar Assembly of N,N'-Bis(4-substituted benzyl)sulfamides", *J. Am. Chem. Soc.121*: 9766-9767 (1999).

Burckhardt, S., "Methyl N-(tricthylammonium-sulfonyl) carbamate: "Burgess Reagent"", *Synlett*: 559 (2000).

Kuang, et al., "Utilization of the 1,2,5-Thiadiazolidin-3-one 1,1-Dioxide Scaffold in the Design of Potent Inhibitors of Serine Proteases: SAR Studies Using Carboxylates", *Bioorg. Med. Chem. 8*: 1005-1016 (2000).

Pete, et al., "Synthesis of 5-Substituted Indole Derviatives, Part II. Synthesis of Sumatriptan through the Japp-Klingermann Reaction", *Heterocycles 53*: 665-673 (2000).

Dougherty, et al., "Ring-Closing Metathesis Strategies to Cyclic Sulfamide Peptidomimetics", *Tetrahedron 56*: 9781-9790 (2000).

Hof, et al., "Emergent Conformational Preferences of a Self-Assembling Small Molecule: Structure and Dynamics in a Tetrameric Capsule", *J. Am. Chem. Soc. 122*: 10991-10996 (2000).

Schaal, et al., "Synthesis and Comparative Molecular Field Analysis (CoMFA) of Symmetric and Nonsymmetric Cyclic Sulfamide HIV-1 Protease Inhibitors", *J. Med. Chem. 44*: 155-169 (2001).

Hof, et al., "Highly slective Synthesis of Heterosubstituted Aromatic Sulfamides", *Organic Letters 3*: 4247-4249 (2001).

Wood, et al., "A novel, one-step method for the conversion of primary alcohols into carbamate-protected amines", *Tetrahedron Lett. 43*: 3887-3890 (2002).

Nicolaou, et al., "A Novel Regio- and Steroselective Synthesis of Sulfamidates from 1,2-Diols Using Burgess and Related Reagents: A Facile Entry into β-Amino Alcohols", *Angew. Chem. Int. Ed. Engl. 41*: 834-838 (2002).

* cited by examiner

Figure 2

| Entry | Starting Material | Product | Yield [%] |
|---|---|---|---|
| 1 | 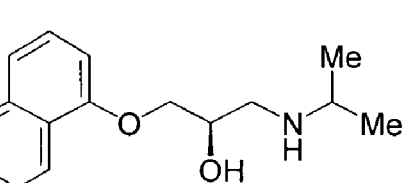 20 | 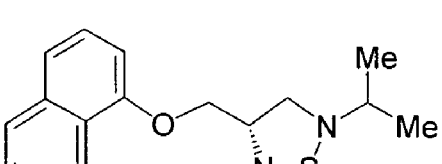 21 | 89[a] |
| 2 | 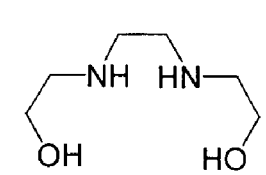 22 | 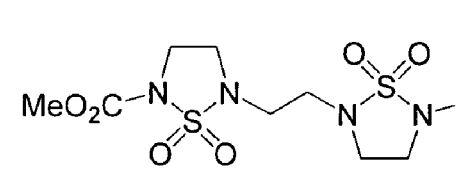 23 | 55[b] |
| 3 | 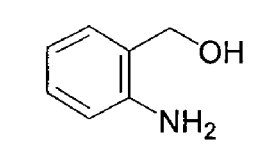 24 | 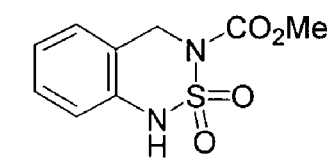 25 | 45[c] |
| 4 | 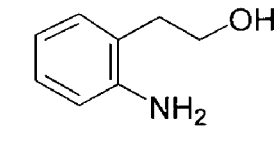 26 | 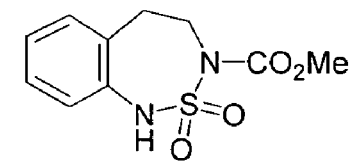 27 | 90[d] |
[a] THF, Δ, 21 h; [b] THF, Δ, 8 h; [c] 0 °C, 1 h, then 25 °C, 5 h; [d] THF, Δ, 2 h.
Figure 3

| Entry | Starting Material | Product | Yield [%] |
|---|---|---|---|
| | H$_2$N-R$^1$(R$^2$)-(CH)$_n$-C(R$^3$)(R$^4$)-OH | cyclic sulfamide with HN-S(O)$_2$-N-CO$_2$Me | |
| 1 | H$_2$N-CH$_2$-CH$_2$-OH (28) | 29 | 62 |
| 2 | H$_2$N-C(Me)$_2$-CH$_2$-OH (30) | 31 | 39 |
| 3 | trans-4-aminocyclohexanol (32) | 33 | 34 |
| 4 | H$_2$N-(CH$_2$)$_3$-OH (34) | 35 | 42 |
| 5 | H$_2$N-CH$_2$-CH(Ph)-OH (36) | 37 | 90[a] |
| 6 | H$_2$N-CH(Ph)-CH(Ph)-OH (38) | 39 | 76[a] |

[a] 0 °C, 1 h, then 25 °C, 5 h.

| Entry | Starting Material | Product | Yield [%] |
|---|---|---|---|
| | $R^1\text{-}N(R^2)\text{-}H$ | Burgess reagent (1), THF, Δ, 2 h → $R^1\text{-}N(R^2)\text{-}S(O)_2\text{-}NH\text{-}CO_2Me$ | |
| 1 | cyclohexyl-NH$_2$ (40) | cyclohexyl-NH-S(O)$_2$-NH-CO$_2$Me (41) | 83 |
| 2 | PhCH$_2$-NH(Me) (42) | PhCH$_2$-N(Me)-S(O)$_2$-NH-CO$_2$Me (43) | 91 |
| 3 | (cyclohexyl)$_2$NH (44) | (cyclohexyl)$_2$N-S(O)$_2$-NH-CO$_2$Me (45) | 82 |
| 4 | morpholine (46) | morpholine-S(O)$_2$-NH-CO$_2$Me (47) | 87 |
| 5 | thiazolidine (48) | thiazolidine-S(O)$_2$-NH-CO$_2$Me (49) | 73 |
| 6 | 4-MeO-C$_6$H$_4$-NH$_2$ (50) | 4-MeO-C$_6$H$_4$-NH-S(O)$_2$-NH-CO$_2$Me (51) | 97 |
| 7 | 4-NC-C$_6$H$_4$-NH$_2$ (52) | 4-NC-C$_6$H$_4$-NH-S(O)$_2$-NH-CO$_2$Me (53) | 66 |
| 8 | (MeO)$_2$CH-CH$_2$-NH$_2$ (54) | (MeO)$_2$CH-CH$_2$-NH-S(O)$_2$-NH-CO$_2$Me (55) | 98[a] |

[a] -10 to 25 °C, 24 h.

| Entry | Starting Material (Yield [%])[a] | Product | Yield [%] |
|---|---|---|---|
| 1 | 17 (82) | 56 | 99[b] |
| 2 | 7 (85) | 57 | 99[b] |
| 3 | 58 (75) | 59 | 97[c] |
| 4 | 60 (82) | 61 | 98[c] |
| 5 | 62 (82) | 63 | 84[d] |
| 6 | 64 (75) | 65 | 87[d] |

Figure 6

SYNTHESIS OF NON-SYMMETRICAL SULFAMIDES USING BURGESS-TYPE REAGENTS

CROSS REFERENCE TO RELATED APPLICATIONS

This is a non-provisional application claiming priority under 35 U.S.C. 119(e) from copending U.S. provisional application Ser. No. 60/417,936, filed Oct. 12, 2002.

STATEMENT OF GOVERNMENT SUPPORT

This invention was made with government support under Contract No. GM63752 by the National Institutes of Health. The Government has certain rights in the invention.

FIELD OF THE INVENTION

The invention is related to the synthesis of N,N'-differentiated sulfamides. More particularly, the invention is related to the synthesis of N,N'-differentiated sulfamides using amino alcohols and simple amines using Burgess-type reagents.

BACKGROUND

Within the realm of proven pharmacophores, the sulfamide functional group (thiadiazine-1,1-dioxide) stands out as one of the most important structural motifs found in high affinity protein ligands and pharmaceutically useful agents. Indeed, a survey of the recent patent literature reveals several hundred proprietary compounds having an impressive and diverse array of biological activities wherein a sulfamide group is incorporated within a suitable scaffold, often cyclic. For examples of such compounds, see R. J. Cherney, et al., 2002, WO-2002028846; N.-Y. Shih, et al., 2001, WO-2001044200; G. M. Benson, et al., 2000, WO-2000076501; R. D. Tung, et al., 1999, U.S. Pat. No. 5,945,413; I. Mcdonald, et al., 1999, WO-9905141. Among the numerous applications of sulfamides, these agents have proven to be particularly effective as inhibitors of key enzymes including HIV protease (W. Schaal, et al., *J. Med. Chem.* 2001, 44, 155–169; Spaltenstein, A.; et al. *Bioorg. Med. Chem. Lett.* 2000, 10, 1159–1162; Bäckbro, K.; et al. *J. Med. Chem.* 1997, 40, 898–902; Hultén, J.; et al. *J. Med. Chem.* 1997, 40, 885–897) and serine protease (Kuang, R.; et al. *Bioorg. Med. Chem.* 2000, 8, 1005–1016; Kuang, R.; et al. *J. Am. Chem. Soc.* 1999, 121, 8128–8129; Groutas, W. C.; et al. *Bioorg. Med. Chem. Lett.* 1999, 9, 2199–2204; Groutas, W. C.; et al. *Bioorg. Med. Chem.* 1998, 6, 661–671), and have demonstrated utility as both agonists and antagonists of critical molecular receptors such as those used to regulate endogenous levels of seratonin (Castro, J. L.; et al. *J. Med. Chem.* 1994, 37, 3023–3032) and histamine (Tozer, M. J.; et al. *Bioorg. Med. Chem. Lett.* 1999, 9, 3103–3108). Beyond their obvious significance in the treatment of disease, cyclic sulfamides have also been employed with considerable success as chiral ligands and auxiliaries (Pansare, S. V.; et al. *Synlett* 1998, 623–624; Ahn, K. H.; et al. *Tetrahedron Lett.* 1992, 33, 6661–6664; Sartor, D.; et al. *Tetrahedron: Asymmetry* 1991, 2, 639–642; Oppolzer, W.; et al. *Tetrahedron Lett.* 1991, 32, 4893–4896; Oppolzer, W.; et al. *Tetrahedron Lett.* 1991, 32, 61–64), and constitute an increasingly popular set of building blocks within the field of supramolecular chemistry (Hof, F.; et al. *Org. Lett.* 2001, 3, 4247–4249; Hof, F.; et al. *J. Am. Chem. Soc.* 2000, 122, 10991–10996; Gong, B.; et al. *J. Am. Chem. Soc.* 1999, 121, 9766–9767 and references cited in each).

Despite the indisputable utility of these compounds, however, existing routes for their synthesis, particularly in a cyclic setting, are far from ideal. For example, typical procedures to fashion cyclosulfamides rely upon the reaction of a diamine with either $SO_2Cl_2$ or $H_2NSO_2NH_2$ at elevated temperatures (Preiss, M. *Chem. Ber.* 1978, 111, 1915–1921; Rosenberg, S. H.; et al. *J. Med. Chem.* 1990, 33, 1582–1590; Dewynter, G.; et al. *Tetrahedron Lett.* 1991, 32, 6545–6548), conditions which often lead to a low yield of product due to the concomitant formation of polycondensation side-products. Equally problematic is the relative scarcity of suitable diamines for these reactions from commercial sources and the difficulties associated with their laboratory preparation. An online search of the available chemicals directory revealed just slightly more than 200 unsubstituted 1,2-diamine substrates. By contrast, there are over 3000 unsubstituted β-amino alcohols. While these issues have led to the development of several alternative protocols for sulfamide synthesis (Tozer, M. J.; et al. *Bioorg. Med. Chem. Lett.* 1999, 9, 3103–3108; Dougherty, J. M.; et al. *Tetrahedron* 2000, 56, 9781–9790; Dewynter, G.; et al. *Tetrahedron Lett.* 1997, 38, 8691–8694.), these additional synthetic technologies have proven amenable only to specific substrate classes and have not yet alleviated the need for multi-step protocols. Most significantly, none of these methods has enabled the efficient and selective synthesis of non-symmetrical N,N'-disubstituted cyclosulfamides (IV, FIG. 1), perhaps the most versatile class of these compounds for generating pharmaceutically-relevant molecular diversity.

What is needed is a general and widely applicable solution for the synthesis of these diverse classes of sulfamides for enabling the reliable and efficient formation of this highly desirable structural moiety (IV).

SUMMARY

A practical and high-yielding method for the efficient, one-step synthesis of diverse classes of N,N'-differentiated sulfamides employs a wide range of amino alcohols and simple amines using Burgess-type reagents. This synthetic technology constitutes a marked improvement over those currently in the literature, and extends the potential applications of sulfamides not only within chemical biology and medicinal chemistry, but also in the fields of asymmetric synthesis and supramolecular chemistry. At a more fundamental level, this methodology serves to delineate new pathways in which the power of the Burgess reagent and its relatives can be applied to effect transformations of critical importance in chemical synthesis.

One aspect of the invention is directed to a process for the synthesizing a mono-protected, non-symmetrical cyclic sulfamide III from an amino alcohol I and Burgess reagent II represented by the following structures:

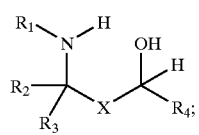

I

-continued

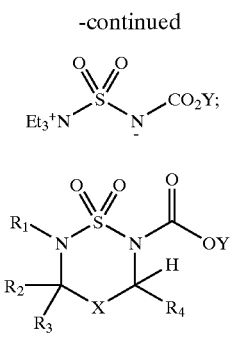

In the first step of the process, a solution of the amino alcohol I in a non-reactive solvent is contacted with a quantity of the Burgess reagent II under reaction conditions for producing sulfamide III. Then, after consuming amino alcohol I, the reaction is neutralized by dilution with a non-reactive solvent and treatment with an aqueous solution. Then, sulfamide III is isolated. In the above structures, X is absent or is a diradical selected from the group consisting of the following structures:

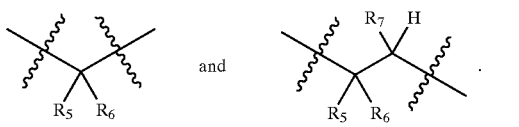

$R_1$ is a radical selected from the group consisting of hydrogen, $C_1$–$C_6$ alkyl, aryl, heteroaryl, alkylaryl, and benzyl, or is a diradical forming a ring with $R_2$; $R_2$ is a radical selected from the group consisting of hydrogen, $C_1$–$C_6$ alkyl, aryl, heteroaryl, alkylaryl, and benzyl, or is a diradical forming a ring with $R_1$ or $R_3$ or $R_4$, or is a diradical forming a part of an aromatic ring with $R_5$; $R_3$ is a radical selected from the group consisting of hydrogen, $C_1$–$C_6$ alkyl, aryl, heteroaryl, alkylaryl, and benzyl, or is a diradical forming a ring with $R_1$ or $R_2$ or $R_5$ or is a diradical forming half of a π-bond with $R_6$; $R_4$ is a radical selected from the group consisting of hydrogen, $C_1$–$C_6$ alkyl, aryl, heteroaryl, and benzyl or is a diradical forming a ring with $R_2$ or with $R_5$; $R_5$ is a radical selected from the group consisting of hydrogen, $C_1$–$C_6$ alkyl, aryl, heteroaryl, alkylaryl, and benzyl, or is a diradical forming a ring with $R_1$ or $R_2$ or $R_6$ or is a diradical forming part of an aromatic ring with $R_3$; $R_6$ is a radical selected from the group consisting of hydrogen, $C_1$–$C_6$ alkyl, aryl, heteroaryl, alkylaryl, and benzyl, or is a diradical forming a ring with $R_1$ or $R_2$ or $R_5$ or is a diradical forming half of a π-bond as part of an aromatic ring with $R_3$; $R_7$ is a radical selected from the group consisting of hydrogen, $C_1$–$C_6$ alkyl, aryl, heteroaryl, alkylaryl, and benzyl; Y is a radical selected from the group consisting of —$CH_3$, —$CH_2Ph$ and —$CH_2CH$=$CH_2$. The following provisos apply: If $R_2$ and $R_5$ are part of an aromatic ring; then $R_3$ and $R_6$ make up a full π-bond; and if X is absent, then $R_3$ cannot be half of a π-bond and $R_2$ is not part of an aromatic ring. In a preferred mode, the quantity of Burgess reagent II is 2.5 equivalents. In an alternative preferred mode, X is absent. In another alternative preferred mode, X is a diradical with the following structure:

In another alternative preferred mode, X is a diradical with the following structure:

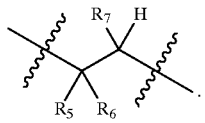

Another aspect of the invention is directed to a process for synthesizing a mono-protected, non-symmetrical sulfamide V from an amine IV and Burgess reagent II represented by the following structures:

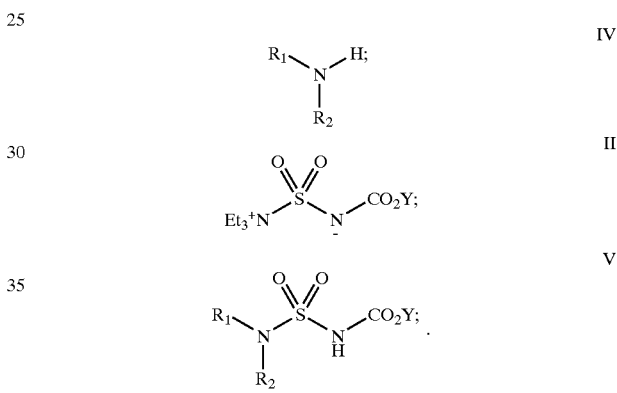

In the first step of the process, a solution of the amine IV is contacted with a quantity of Burgess reagent II for under reaction conditions for producing sulfamide V. Then, the reaction his neutralized by dilution with a non-reactive solvent and treatment with an aqueous solution. Then, the sulfamide V is isolalted. In the above structures, $R_1$ is a radical selected from the group consisting of hydrogen, $C_1$–$C_6$ alkyl, aryl, heteroaryl, alkylaryl, and benzyl, or a diradical forming a ring with $R_2$; $R_2$ is a radical selected from the group consisting of hydrogen, $C_1$–$C_6$ alkyl, aryl, heteroaryl, alkylaryl, and benzyl, or a diradical forming a ring with $R_1$; and Y is a radical selected from the group consisting of —$CH_3$, —$CH_2Ph$ and —$CH_2CH$=$CH_2$. In a preferred mode, the quantity of Burgess reagent II is 1.25 equivalents.

BRIEF DESCRIPTION OF FIGURES

FIG. 2 illustrates a chart showing the synthesis of a variety of non-symmetrical five-membered ring cyclic sulfamides from b-amino alcohols using the Burgess reagent 1.

FIG. 3 illustrates a table showing the synthesis of non-symmetrical cyclic sulfamides from precursor amino alcohols using Burgess reagent (1).

FIG. 4 illustrates a table showing the synthesis of mono-protected cyclic sulfamides from precursor primary amino alcohols using Burgess reagent (1).

FIG. 5 illustrates that Burgess reagent (1) can smoothly effect the generation of non-symmetrical, linear sulfamides from all classes of amines in excellent yield (FIG. 5).

FIG. 6 illustrates a table showing the deprotection of cyclic sulfamides to yield non-symmetrical, mono-substituted sulfamides.

DETAILED DESCRIPTION

Figure 1:
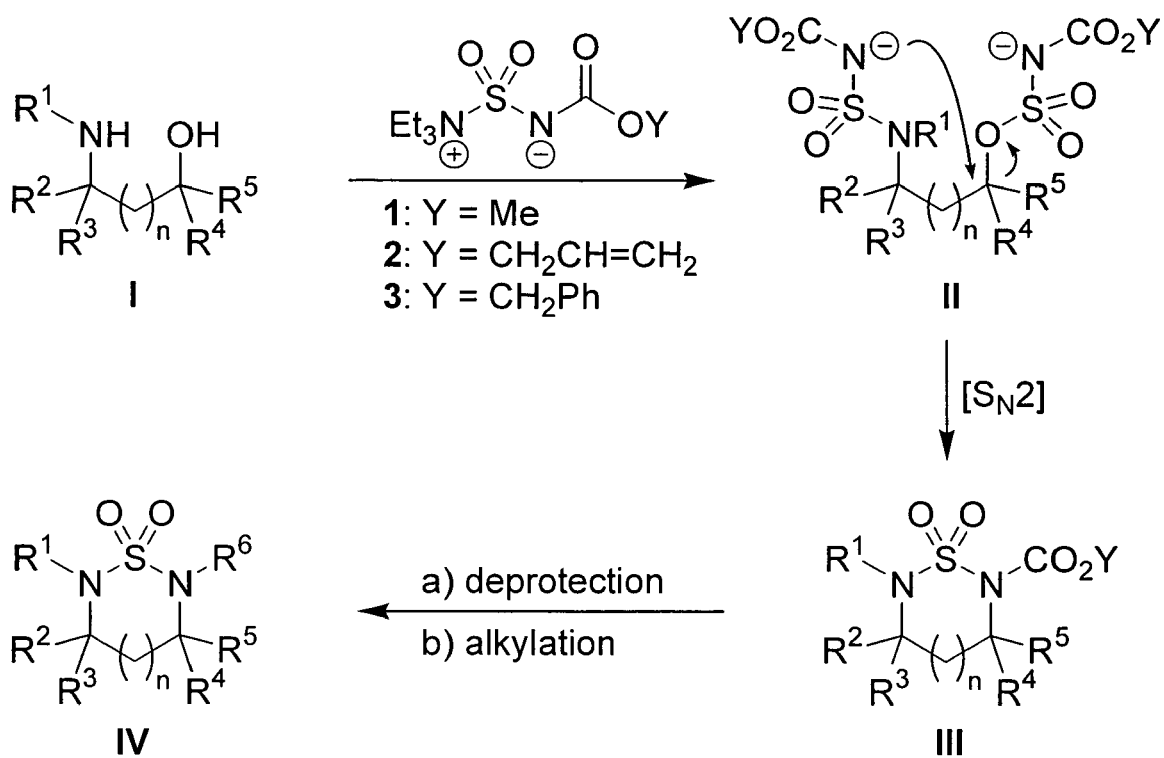
FIG. 1 illustrates a conversion of amino alcohols (I) to cyclic sulfamides (III) using Burgess (1) and related reagents (2 and 3) and further elaboration leading to non-symmetrically substituted, structurally diverse products (IV).

K. C. Nicolaou, et al. disclosed that β-amino alcohols can be smoothly synthesized with excellent chiral integrity from precursor diols through a novel cyclization reaction initiated by Burgess reagent (1, FIG. 1) (Atkins, G. M.; Burgess, E. M. *J. Am. Chem. Soc.* 1968, 90, 4744–4745; Atkins, G. M.; Burgess, E. M. *J. Am. Chem. Soc.* 1972, 94, 6135–6141; Burgess, E. M.; Penton, H. R.; Taylor, E. A. *J. Org. Chem.* 1973, 38, 26–31) and related compounds (2 and 3) (Nicolaou, K. C.; et al. *Angew. Chem.* 2002, 114, 862–866; *Angew. Chem. Int. Ed.* 2002, 41, 834–838). It is disclosed herein that, upon application of this protocol to an amino alcohol starting material (I), a mono-protected, non-symmetrical cyclic sulfamide (III) results in a single, stereocontrolled operation through the delineated mechanism (FIG. 1). It is disclosed herein that this reaction course can be successfully realized in preference to the more typical rearrangement/dehydration pathways promoted by these reagents and that subsequent deprotection of the carbamate in III, followed by substitution with an appropriate electrophile, then provides access to an assorted collection of sulfamides (IV) with the potential to incorporate diversity at all possible sites. For references that disclose more typical rearrangement/dehydration pathways, see P. Taibe, S. Mobashery in *Encyclopedia of Reagents for Organic Synthesis*, Vol. 5 (Ed.: L. A. Paquette), John Wiley & Sons: Chichester, 1995, pp. 3345–3347; and S. Burckhardt, *Synlett* 2000, 559. Also, for some additional primary literature, see: Burgess, E. M.; Penton, H. R.; Taylor, E. A. *J. Am. Chem. Soc.* 1970, 92, 5224–5226; Wood, M. R.; Kim, J. Y.; Books, K. M. *Tetrahedron Lett.* 2002, 43, 3887–3890.)

To demonstrate this teaching, the methodology was employed using a representative set of commercially available secondary β-amino alcohols. Exposure of all substrates listed in FIG. 2 to excess Burgess reagent (1) in refluxing THF for 8 hours led to the formation of the desired cyclic sulfamide product in high yield, regardless of the nature of the group attached onto the amine. Of particular note, neither placing the amine in a hindered cyclic setting (entry 4) nor adding a bulky t-butyl substituent (entry 3) retarded product formation; this latter substrate constitutes a particularly effective test for the power of this synthetic technology, as starting materials bearing this functionality have, in general, proven recalcitrant to sulfamide formation with currently available methods (Castro, J. L.; et al. *J. Med. Chem.* 1994, 37, 3023–3032). Of equal importance, all aniline-derived systems (entries 5–8) proved readily amenable to the cyclization process regardless of the electron-withdrawing (entries 6 and 7) or donating (entry 8) properties of the appended aromatic ring. These results are particularly indicative of the broad versatility of this intramolecular Burgess-mediated cyclization, i.e., they demonstrate that the methodology may be employed in circumstances wherein the two nitrogen atoms of the sulfamide product are effectively differentiated. (Note: Amino alcohol substrates 14, 16, and 18 were prepared by the method of Heine, H. W.; et al. *J. Am. Chem. Soc.* 1954, 76, 2503. For alternative approaches to fashion these compounds, see: Rudesill, J. T.; et al. *J. Org. Chem.* 1971, 36, 3071–3076.)

The limits of the Burgess-mediated sulfamide synthesis are more fully disclosed by the use of more challenging substrates. As shown in FIG. 3, employing a chiral secondary alcohol (entry 1), even in a relatively hindered context, failed to engender any particular difficulties (although extension of the reaction time beyond the standard 8 hours of heating was required to optimize yields), leading to 21 with clean inversion of configuration. A double cyclization seeking to generate a bis-sulfamide (23, entry 2) was also smoothly effected, with reduced yield in this case solely due to difficulties encountered during isolation of this polar product. Finally, following optimization of the reaction conditions, extension of the sulfamide cyclization to ring sizes beyond the five-membered products formed in the previous examples also proved to be possible. Initial efforts in this regard focused on 24 (entry 3), wherein commencing the reaction at 0° C. for 1 hour then warming to ambient temperature for 5 hours led to the desired product (25) in 45% yield. All other conditions examined provided no improvement on this yield, giving only greater amounts of decomposition and leading us to conclude that the activated primary benzylic alcohol was responsible. Fundamentally, however, the formation of other sulfamide-containing rings should not prove to be as problematic if a non-benzylic alcohol is employed instead. For this reason, phenethylalcohol 26 was examined and it was shown that the seven-membered ring analog (27, entry 4) was readily generated in 90% yield through a cyclization reaction that is less favorable both enthalpically and entropically than that to form a six-membered ring. The smooth generation of 27 is additionally significant because this bicyclic product is analogous to the benzodiazepine motif, a molecular scaffold that has been the subject of intensive biological investigations and the source of several clinically-employed agents (The literature pertaining to this field is so vast that it even has its own journal entitled *Benzodiazepine*. For additional general references, see information contained within: *Comprehensive Medicinal Chemistry* (Eds.: C. Hansch, P. G. Sammes, J. B. Taylor), Pergamon: Oxford, 1990). In view of the successful cyclization of the latter two primary aryl amine substrates in FIG. 3, further extensions of this methodology were desired.

It is further disclosed that both sides of the resultant sulfamide product can be substituted in turn, leading to greater structural diversity. However, it is not preferred to employed primary aliphatic amino alcohols to this end. All four substrates examined within this class (entries 1–4, FIG. 4) gave rather disappointing yields of sulfamide products, leading either to decomposition or to the formation of side-products resulting from undesired rearrangements. In retrospect, however, the poor performance of these substrates in an intramolecular cyclization relative to their secondary amine counterparts is not so surprising, as in the absence of an additional alkyl or aryl substituent, the nitrogen atom is less nucleophilic, requiring a longer reaction time and providing a greater opportunity for decomposition/rearrangement. The modest yields observed in these examples, however, do not really constitute a limitation in strategy, as the quantitative debenzylation of 7 (entry 2, FIG. 2) using Pearlman's catalyst provided a route to the same product 29 (entry 1, FIG. 4), thus alleviating the need to start with ethanolamine (28). As such, this approach provides a tactic to sequentially substitute both sides of any cyclic sulfamide product, if so desired. Finally, in contrast with the results in the rest of FIG. 4, when primary aliphatic amines were utilized in conjunction with a secondary benzylic alcohol (entries 5 and 6, FIG. 4), product yields were good when the reaction was performed at low temperature. As such, these unanticipated results suggest that there is a subtle interplay between substrate structure and particular reaction conditions to facilitate sulfamide formation in synthetically useful yield.

Beyond the synthesis of cyclic sulfamides, it is also disclosed herein that Burgess reagent (1) can smoothly effect the generation of non-symmetrical, linear sulfamides from all classes of amines in excellent yield (FIG. 5). While this same conversion is more typically achieved by adding the amine to an appropriate chlorosulfonylisocyanate derivative, the present conditions provide a mild alternative which avoids the use of these rather toxic and corrosive agents directly on the reaction substrate. For examples of the use of chlorosulfonylisocyanate derivatives, see Tozer, M. J.; et al., viz. *Bioorg. Med. Chem. Lett.* 1999, 9, 3103–3108; For an alternative synthesis of linear sulfamides, see, Davis, F. A.; et al.; *Tetrahedron Lett.* 1986, 27, 3957–3960.

All of the preceding examples of sulfamide synthesis in FIGS. 2–5 led to products with methyl carbamate protection. Accordingly, the Cbz and Alloc Burgess-type reagents (2 and 3, FIG. 1) reported by Nicolaou et al. (Nicolaou, K. C.; et al. *Angew. Chem.* 2002, 114, 862–866; *Angew. Chem. Int. Ed.* 2002, 41, 834– 838) were characterized with respect to their ability to perform the same transformations. All of the Burgess-type reagents reported by Nicolaou et al., including 2 and 3, were readily isolable, and were purified through trituration with toluene and then stored at 0° C. for several months. (Note: The recent use of 3 in solution by a Merck group, (Wood, M. R.; Kim, J. Y.; Books, K. M. *Tetrahedron Lett.* 2002, 43, 3887–3890), does not indicate that these reagents are unnstable in the solid form.) In all cases examined, these reagents provided the desired product in yields that were equivalent to those obtained with the original Burgess reagent (1). As such, this method of sulfamide synthesis, whether for cyclic or linear systems, can be tailored with a variety of protecting groups to fit the particular needs of the test molecule. In line with several reports (Pete, B.; et al. *Heterocycles* 2000, 53, 665–673), it is also disclosed herein that subsequent deprotection (see FIG. 6) is easily achieved with conventional procedures and readily followed by substitution of appropriate electrophiles (see Experimental Section). As such, the general and efficient synthesis of compounds represented by structure IV (FIG. 1) has been realized.

Experimental Section

Representative Procedure:

The desired Burgess reagent (1–3, 1.25 mmol, 2.5 equiv) was added in one portion to a stirred solution of amino alcohol (0.5 mmol, 1.0 equiv) in THF (2 mL). The reaction mixture was then subjected to the conditions defined in the Figures. Upon completion, the reaction was diluted with $CH_2Cl_2$ (20 mL) and washed with 1N HCl (30 mL). The aqueous phase was re-extracted with $CH_2Cl_2$ (2×20 mL) and the combined organic phase was dried ($Na_2SO_4$), filtered, and concentrated. Flash column chromatography on silica gel then provided the desired products in the yields quoted.

Detailed Description of Figures

FIG. 1 shows the proposed conversion of amino alcohols (I) to cyclic sulfamides (III) using Burgess (1) and related reagents (2 and 3) and further elaboration leading to non-symmetrically substituted, structurally diverse products (IV). The sulfanamide nitrogen displaces the activated hydroxyl with inversion of configuration in clean SN2 fashion. Further functionalization is possible for product III.

Figure 2:
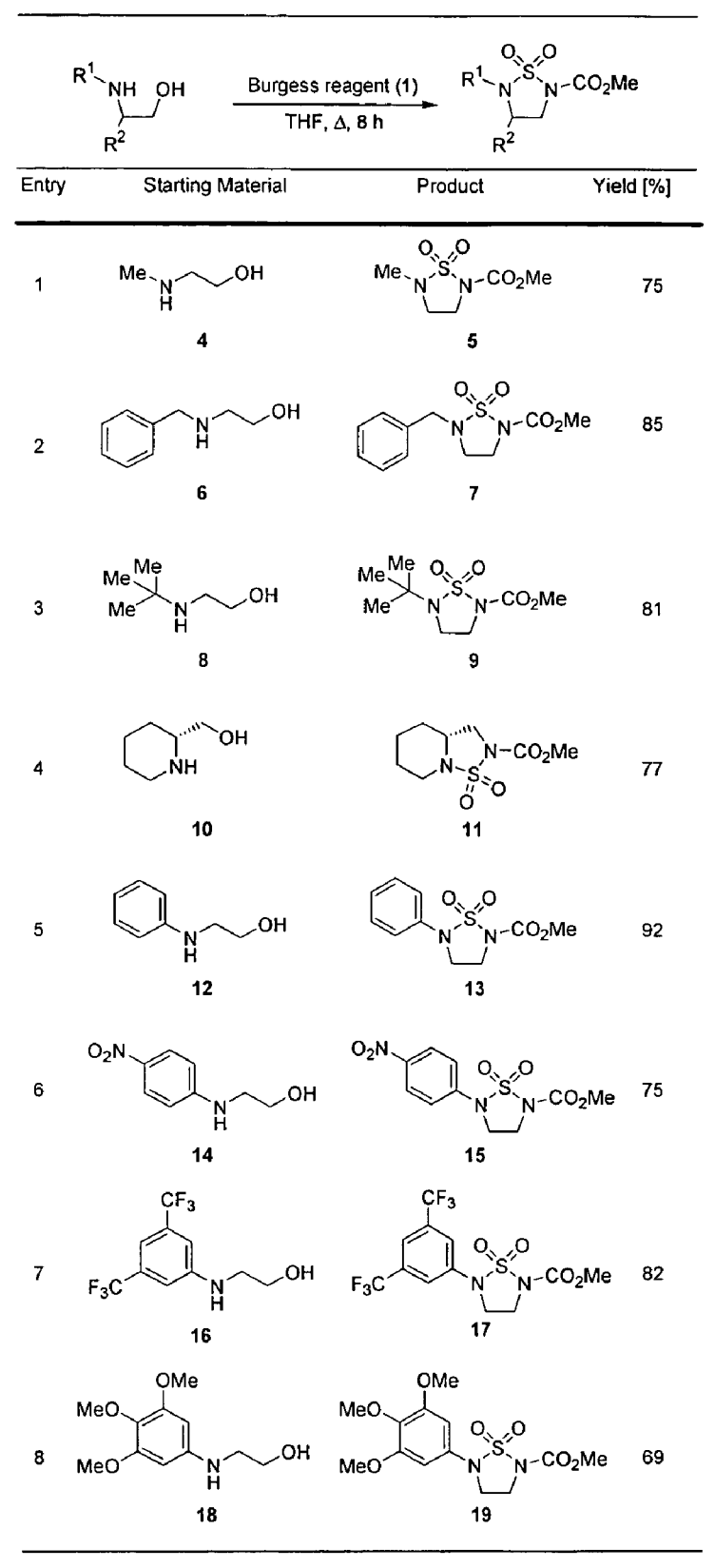

FIG. 2 is a chart showing the synthesis of a variety of non-symmetrical five-membered ring cyclic sulfamides from b-amino alcohols using the Burgess reagent 1. A representative set of commercially available secondary β-amino alcohols was investigated. Exposure of all substrates listed in FIG. 2 to excess Burgess reagent (1) in refluxing THF for 8 hours led to the formation of the desired cyclic sulfamide product in high yield, regardless of the nature of the group attached onto the amine. Of particular note, neither placing the amine in a hindered cyclic setting (entry 4) nor adding a bulky t-butyl substituent (entry 3) retarded product formation. All aniline-derived systems (entries 5–8) proved readily amenable to the cyclization process regardless of the electron-withdrawing (entries 6 and 7) or donating (entry 8) properties of the appended aromatic ring, results indicative of the versatility of this intramolecular Burgess-mediated cyclization.

FIG. 3 is a table showing the synthesis of non-symmetrical cyclic sulfamides from precursor amino alcohols using Burgess reagent (1). Here there was exploration of additional substrate classes and development of optimized reaction conditions. Employing a chiral secondary alcohol (entry 1, 20) failed to produce any particular difficulties (although extension of the reaction time beyond the standard 8 hours of heating was required to optimize yields), leading to 21 with clean inversion of configuration.

FIG. 4 is a table showing the synthesis of mono-protected cyclic sulfamides from precursor primary amino alcohols using Burgess reagent (1). All four substrates examined within this class (entries 1–4) gave rather disappointing yields of sulfamide products, leading either to decomposition or to the formation of side-products resulting from undesired rearrangements. The poor performance of these substrates in an intramolecular cyclization relative to their secondary amine counterparts is not so surprising, as in the absence of an additional alkyl or aryl substituent, the nitrogen atom is less nucleophilic, requiring a longer reaction time and providing a greater opportunity for decomposition/rearrangement.

FIG. 5 shows that Burgess reagent (1) can smoothly effect the generation of non-symmetrical, linear sulfamides from all classes of amines in excellent yield (FIG. 5). While this same conversion is more typically achieved by adding the amine to an appropriate chlorosulfonylisocyanate derivative (Tozer, M. J.; et al. *Bioorg. Med. Chem. Lett.* 1999, 9, 3103–3108; these conditions provide a mild alternative which avoids the use of these rather toxic and corrosive agents directly on the reaction substrate. In this case, only 1.3 equivalents of Burgess reagent is used to facilitate the reaction process.

FIG. 6 is a table showing the deprotection of cyclic sulfamides to yield non-symmetrical, mono-substituted sulfamides. (a) Yield in parentheses is that for synthesis of the starting material; (b) NaOH, MeOH:$H_2O$ (2:1), 25° C., 2 hours; (c) Pd(OAc)$_2$ (10 mol %), 3,3',3"-phosphinidynetris (benzenesulfonic acid) trisodium salt (20 mol %), HNEt$_2$ (40 equiv), MeCN:H$_2$O (1:1), 25° C., 15 min; (d) 10% Pd/C, H$_2$ (60 psi), EtOH:EtOAc (4:1), 25° C., 2 hours.

Figure 7:
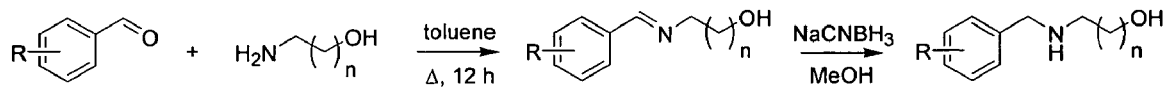
FIG. 7 is a table showing the synthesis of cyclic sulfamides by refluxing the starting material and reagent in THF for two hours.

FIG. 7 is a table showing the synthesis of cyclic sulfamides by refluxing the starting material and reagent in THF for two hours. The preparation of the substrates is shown at the bottom of the page. Imine formation with the appropriate aromatic aldehyde is followed by reduction with cyanoborohydride to give the desired aminol starting material. All 3 types of rings tested gave good results.

What is claimed is:

1. A process for the synthesizing a mono-protected, non-symmetrical cyclic sulfamide III from an amino alcohol I and Burgess reagent II represented by the following structures:

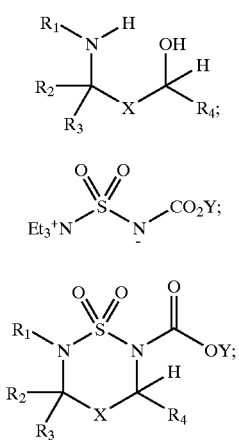

the process comprising the following steps:
    Step A: contacting a solution of the amino alcohol I in a non-reactive solvent with a quantity of the Burgess reagent II for producing sulfamide III; then, after consuming amino alcohol I
    Step B: neutralizing the reaction of said Step A by dilution with a non-reactive solvent and treatment with an aqueous solution; and then
    Step C: isolating sulfamide III;
wherein:
    X is absent or is a diradical selected from the group consisting of the following structures:

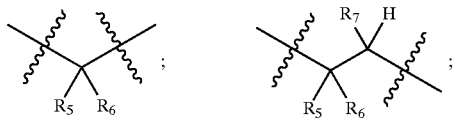

R$_1$ is a radical selected from the group consisting of hydrogen, C$_1$–C$_6$ alkyl, aryl, heteroaryl, alkylaryl, and benzyl, or is a diradical forming a ring with R$_2$;
    R$_2$ is a radical selected from the group consisting of hydrogen, C$_1$–C$_6$ alkyl, aryl, heteroaryl, alkylaryl, and benzyl, or is a diradical forming a ring with R$_1$ or R$_3$ or R$_4$, or is a diradical forming a part of an aromatic ring with R$_5$;
    R$_3$ is a radical selected from the group consisting of hydrogen, C$_1$–C$_6$ alkyl, aryl, heteroaryl, alkylaryl, and benzyl, or is a diradical forming a ring with R$_1$ or R$_2$ or R$_5$ or is a diradical forming half of a π-bond with R$_6$;
    R$_4$ is a radical selected from the group consisting of hydrogen, C$_1$–C$_6$ alkyl, aryl, heteroaryl, and benzyl or is a diradical forming a ring with R$_2$ or with R$_5$;
    R$_5$ is a radical selected from the group consisting of hydrogen, C$_1$–C$_6$ alkyl, aryl, heteroaryl, alkylaryl, and benzyl, or is a diradical forming a ring with R$_1$ or R$_2$ or R$_6$ or is a diradical forming part of an aromatic ring with R$_3$;
    R$_6$ is a radical selected from the group consisting of hydrogen, C$_1$–C$_6$ alkyl, aryl, heteroaryl, alkylaryl, and benzyl, or is a diradical forming a ring with R$_1$ or R$_2$ or R$_5$ or is a diradical forming half of a π-bond as part of an aromatic ring with R$_3$;
    R$_7$ is a radical selected from the group consisting of hydrogen, C$_1$–C$_6$ alkyl, aryl, heteroaryl, alkylaryl, and benzyl;
    Y is a radical selected from the group consisting of —CH$_3$, —CH$_2$Ph and —CH$_2$CH=CH$_2$;
with the following proviso:
    if R$_2$ and R$_5$ are part of an aromatic ring; then R$_3$ and R$_6$ make up a full π-bond;
    if X is absent, then R$_3$ cannot be half of a π-bond and R$_2$ is not part of an aromatic ring.

2. A process according to claim 1 where the quantity of Burgess reagent II is 2.5 equivalents.

3. A process according to claim 2 where X is absent.

4. A process according to claim 2 where X is a diradical with the following structure:

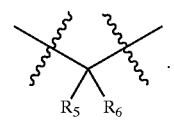

5. A process according to claim 2 where X is a diradical with the following structure:

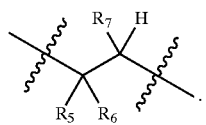

6. A process for synthesizing a mono-protected, non-symmetrical sulfamide V from an amine IV and Burgess reagent II represented by the following structures:

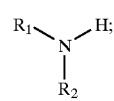

-continued

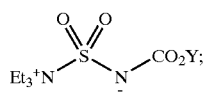

II

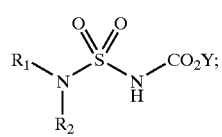

V the process comprising the following steps:
Step A: contacting a solution of the amine IV with a quantity of Burgess reagent II for producing sulfamide V; then Step B: neutralizing the reaction of said Step A by dilution with a non-reactive solvent and treatment with an aqueous solution; and then Step C: isolating the sulfamide V;

wherein:
$R_1$ is a radical selected from the group consisting of hydrogen, $C_1$–$C_6$ alkyl, aryl, heteroaryl, alkylaryl, and benzyl, or a diradical forming a ring with $R_2$;

$R_2$ is a radical selected from the group consisting of hydrogen, $C_1$–$C_6$ alkyl, aryl, heteroaryl, alkylaryl, and benzyl, or a diradical forming a ring with $R_1$; and Y is a radical selected from the group consisting of —$CH_3$, —$CH_2Ph$ and —$CH_2CH$=$CH_2$.

7. A process according to claim 6 wherein the quantity of Burgess reagent II is 1.25 equivalents.

* * * * *